(12) United States Patent
Biedermann et al.

(10) Patent No.: US 10,182,848 B2
(45) Date of Patent: Jan. 22, 2019

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 713 days.

(21) Appl. No.: 14/517,624

(22) Filed: Oct. 17, 2014

(65) Prior Publication Data
US 2016/0045228 A1 Feb. 18, 2016

Related U.S. Application Data

(63) Continuation of application No. 12/709,375, filed on Feb. 19, 2010, now Pat. No. 8,926,671.
(Continued)

(30) Foreign Application Priority Data

Feb. 20, 2009 (EP) .................................... 09002468

(51) Int. Cl.
*A61B 17/70* (2006.01)
*A61B 17/56* (2006.01)

(52) U.S. Cl.
CPC ...... *A61B 17/7037* (2013.01); *A61B 17/7032* (2013.01); *A61B 2017/564* (2013.01)

(58) Field of Classification Search
CPC . A61B 17/70; A61B 17/7032; A61B 17/7034; A61B 17/7037
See application file for complete search history.

(56) References Cited

U.S. PATENT DOCUMENTS

| 5,672,176 A | 9/1997 | Biedermann et al. |
| 6,010,503 A | 1/2000 | Richelsoph et al. |
| (Continued) | | |

FOREIGN PATENT DOCUMENTS

| CN | 1359660 A | 7/2002 |
| EP | 0 947 174 A2 | 10/1999 |
| (Continued) | | |

OTHER PUBLICATIONS

European Search Report for European Application No. 09002468.8, Applicant Biedermann Motech GmbH, European Search Report dated May 5, 2009 and dated May 18, 2009 (6 pgs.).
(Continued)

*Primary Examiner* — Anu Ramana
(74) *Attorney, Agent, or Firm* — Lewis Roca Rothgerber Christie LLP

(57) ABSTRACT

A receiving part for receiving a rod for coupling the rod to a bone anchoring element, the receiving part including: a receiving part body having a channel for receiving a rod and defining an accommodation space for accommodating a head of a bone anchoring element, the accommodation space having an opening for inserting the head; and a pressure element at least partially in the accommodation space, the pressure element including a first portion having a recess to receive the rod, and a second portion having a flexible portion to clamp the head, wherein the pressure element is moveable along a longitudinal axis of the receiving part body from an inserting position to insert the head, to a pre-locking position to clamp the head in the receiving part
(Continued)

by a pre-stress exerted by the pressure element, to a locking position to lock the head in the receiving part.

24 Claims, 8 Drawing Sheets

Related U.S. Application Data

(60) Provisional application No. 61/154,306, filed on Feb. 20, 2009.

(56) References Cited

U.S. PATENT DOCUMENTS

| | | | |
|---|---|---|---|
| 6,063,090 | A | 5/2000 | Schläpfer |
| 6,132,432 | A | 10/2000 | Richelsoph |
| 6,355,040 | B1 | 3/2002 | Richelsoph et al. |
| 6,368,321 | B1 | 4/2002 | Jackson |
| 6,471,705 | B1 | 10/2002 | Biedermann et al. |
| 7,144,396 | B2 | 12/2006 | Shluzas |
| 7,291,151 | B2 | 11/2007 | Alvarez |
| 7,322,981 | B2 | 1/2008 | Jackson |
| 7,604,655 | B2 | 10/2009 | Warnick |
| 7,682,377 | B2 | 3/2010 | Konieczynski et al. |
| 8,083,776 | B2 | 12/2011 | Alvarez |
| 8,444,681 | B2 | 5/2013 | Jackson et al. |
| 8,926,671 | B2 | 1/2015 | Biedermann et al. |
| 2002/0082602 | A1 | 6/2002 | Biedermann et al. |
| 2003/0167058 | A1 | 9/2003 | Shluzas |
| 2005/0137594 | A1 | 6/2005 | Doubler et al. |
| 2006/0089644 | A1 | 4/2006 | Felix |
| 2006/0161153 | A1 | 7/2006 | Hawkes et al. |
| 2006/0173456 | A1 | 8/2006 | Hawkes et al. |
| 2007/0123862 | A1 | 5/2007 | Warnick |
| 2007/0161996 | A1 | 7/2007 | Biedermann et al. |
| 2007/0161999 | A1 | 7/2007 | Biedermann et al. |
| 2007/0270813 | A1 | 11/2007 | Garamszegi |
| 2007/0288004 | A1 | 12/2007 | Alvarez |
| 2008/0009862 | A1 | 1/2008 | Hoffman |
| 2008/0147129 | A1 | 6/2008 | Biedermann et al. |
| 2008/0154315 | A1 | 6/2008 | Jackson |
| 2008/0183215 | A1 | 7/2008 | Altarac et al. |
| 2008/0234761 | A1 | 9/2008 | Jackson |
| 2008/0243193 | A1 | 10/2008 | Ensign et al. |
| 2008/0249576 | A1 | 10/2008 | Hawkes et al. |
| 2008/0269809 | A1 | 10/2008 | Garamszegi |
| 2008/0294202 | A1 | 11/2008 | Peterson et al. |
| 2008/0294203 | A1 | 11/2008 | Kovach et al. |
| 2009/0012567 | A1 | 1/2009 | Biedermann et al. |
| 2009/0018591 | A1 | 1/2009 | Hawkes et al. |
| 2009/0036934 | A1 | 2/2009 | Biedermann et al. |
| 2009/0062865 | A1 | 3/2009 | Schumacher |
| 2009/0062867 | A1 | 3/2009 | Schumacher |
| 2009/0105716 | A1 | 4/2009 | Barrus |
| 2009/0149887 | A1 | 6/2009 | Schlaepfer et al. |
| 2010/0114171 | A1 | 5/2010 | Boachie-Adjei et al. |
| 2010/0137918 | A1 | 6/2010 | Wilcox et al. |
| 2010/0145394 | A1 | 6/2010 | Harvey et al. |
| 2010/0152787 | A1 | 6/2010 | Walsh et al. |
| 2010/0198272 | A1 | 8/2010 | Keyer et al. |
| 2011/0202094 | A1 | 8/2011 | Pereira et al. |
| 2011/0213424 | A1 | 9/2011 | Biedermann et al. |
| 2012/0035670 | A1 | 2/2012 | Jackson et al. |
| 2012/0046701 | A1 | 2/2012 | Gennari et al. |
| 2012/0143266 | A1 | 6/2012 | Jackson et al. |
| 2012/0179210 | A1 | 7/2012 | Garamszegi |
| 2012/0209336 | A1 | 8/2012 | Jackson et al. |
| 2014/0236239 | A1 | 8/2014 | Biedermann et al. |
| 2016/0045228 | A1 | 2/2016 | Biedermann et al. |

FOREIGN PATENT DOCUMENTS

| | | |
|---|---|---|
| EP | 1 749 489 A1 | 2/2007 |
| EP | 1 923 011 A1 | 5/2008 |
| EP | 2 301 458 A1 | 3/2011 |
| JP | 8-257035 | 10/1996 |
| JP | 10-225467 A | 8/1998 |
| JP | 11-318933 | 11/1999 |
| JP | 2001-505469 A | 4/2001 |
| JP | 2007-105472 A | 4/2007 |
| JP | 2008-541880 A | 11/2008 |
| JP | 2011-67628 A | 4/2011 |
| JP | 2013-500127 A | 1/2013 |
| WO | WO 2006/127992 | 11/2006 |
| WO | WO 2007/038350 A2 | 4/2007 |
| WO | WO 2007/117366 A2 | 10/2007 |
| WO | WO 2009/014540 A1 | 1/2009 |
| WO | WO 2011/043805 A1 | 4/2011 |

OTHER PUBLICATIONS

Korean Office action for Application No. 10-2010-0013817, dated Feb. 18, 2016, and English translation (12 pages).

Non-Final Office action for U.S. Appl. No. 14/177,145, dated Apr. 28, 2015, 11 pages.

Final Office action for U.S. Appl. No. 14/177,145, dated Nov. 5, 2015, 11 pages.

Non-Final Office action for U.S. Appl. No. 14/177,145, dated Jul. 5, 2016, 14 pages.

Final Office action for U.S. Appl. No. 14/177,145, dated Dec. 28, 2016, 14 pages.

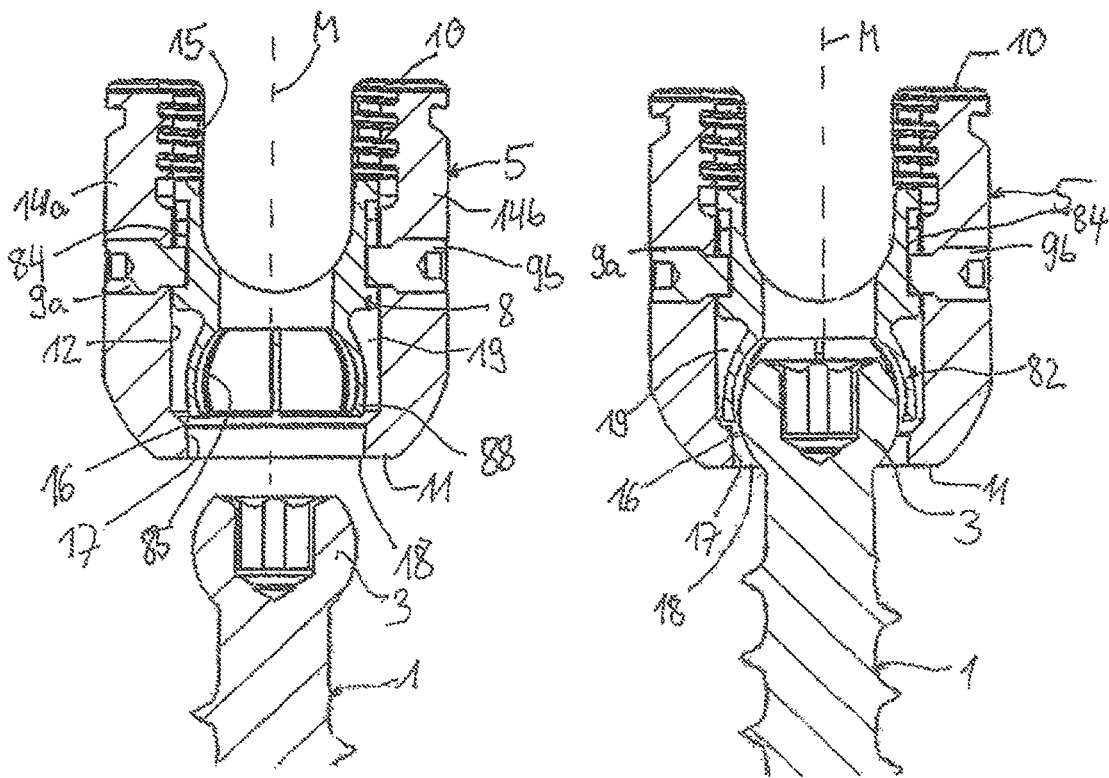

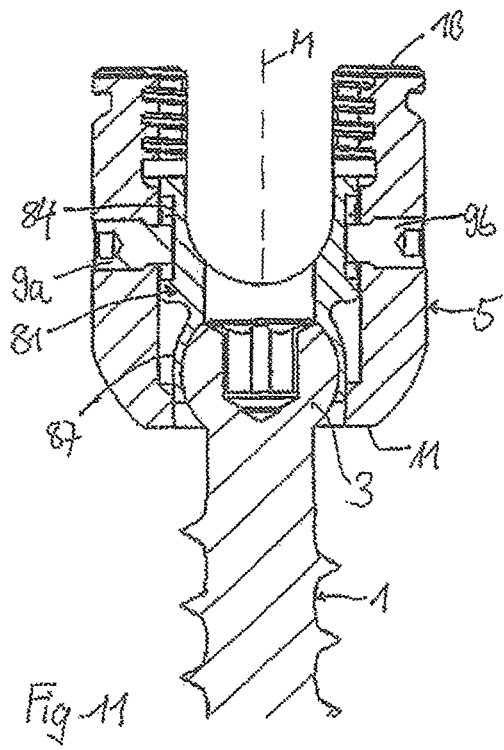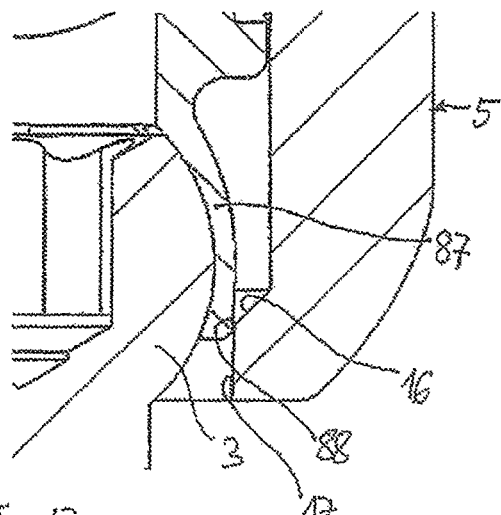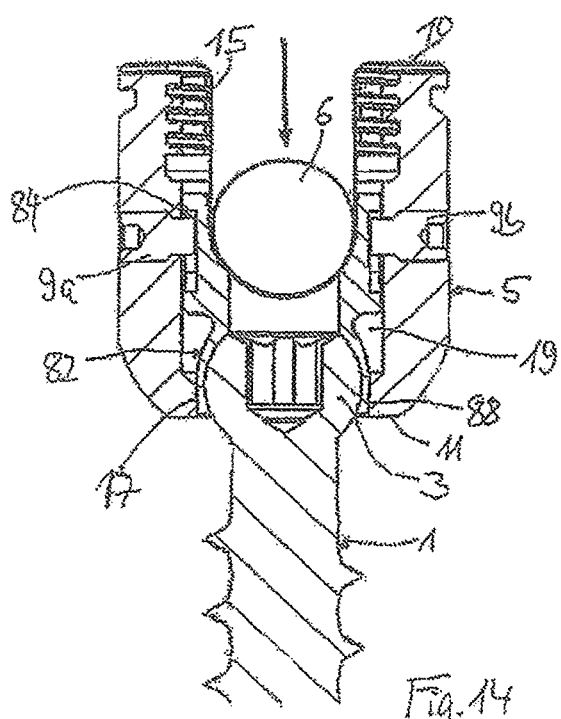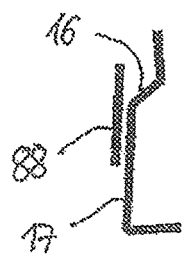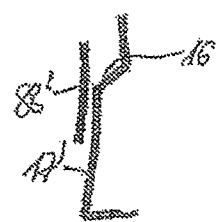

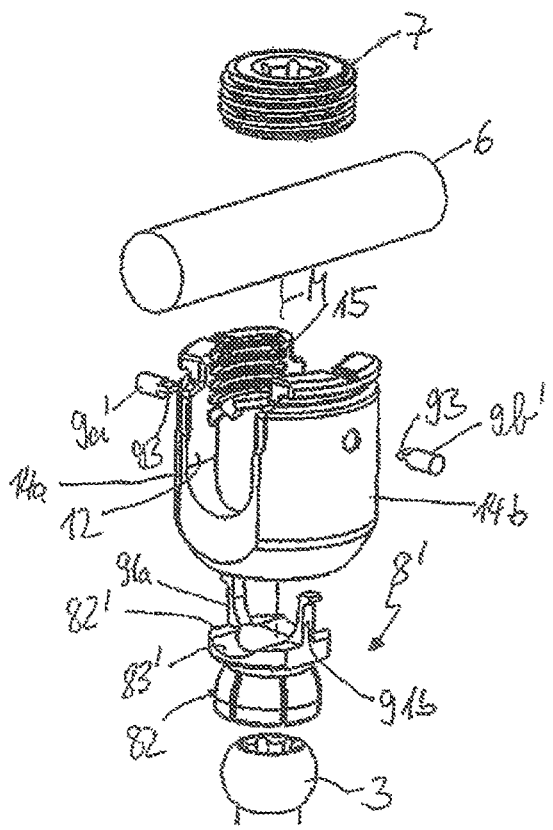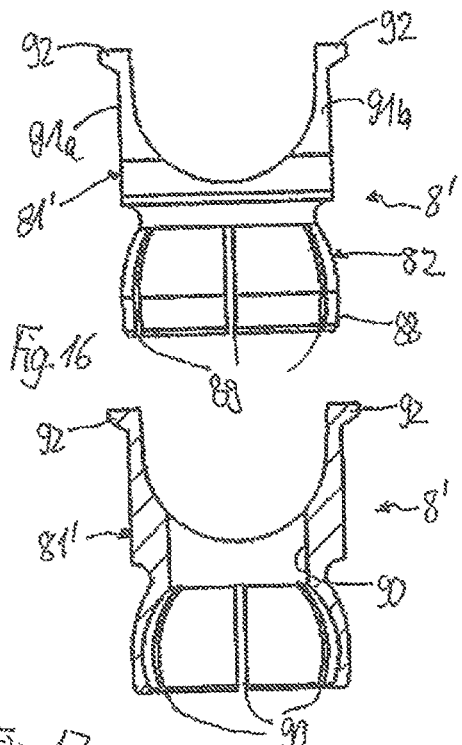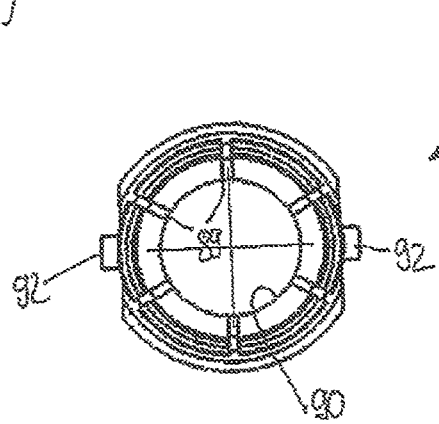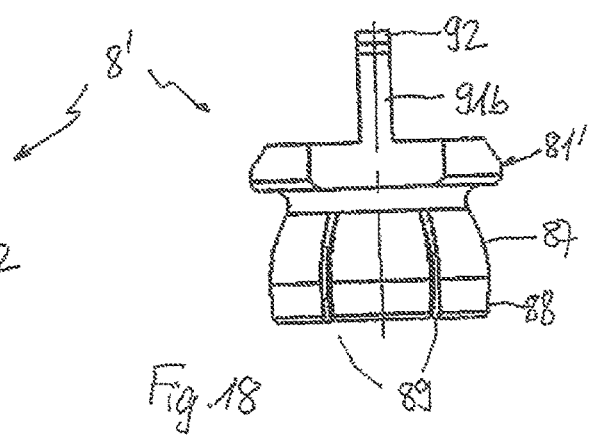

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATION(S)

This application is a continuation of U.S. patent application Ser. No. 12/709,375, filed Feb. 19, 2010, now U.S. Pat. No. 8,926,671, issued Jan. 6, 2015, which claims the benefit of U.S. Provisional Patent Application Ser. No. 61/164,306, filed Feb. 20, 2009, the contents of which are hereby incorporated by reference in their entirety, and claims priority from European Patent Application EP 09 002 468.8, filed Feb. 20, 2009, the contents of which are hereby incorporated by reference in their entirety.

BACKGROUND

Field of the Invention

The invention relates to a receiving part for receiving a rod for coupling the rod to a bone anchoring element and a bone anchoring device with such a receiving part. The receiving part includes a receiving part body and a pressure element located at least partly in an accommodation space of the receiving part body. The pressure element has a flexible portion to clamp the head. The pressure element can assume in the receiving part body an insertion position in which introduction and removal of the head is permitted, a locking position in which the head is locked in the receiving part, and a pre-locking position in which the head is clamped by a pre-stress exerted by the pressure element.

Description of Related Art

Various designs of polyaxial bone screws, wherein the head is clamped from the side to lock the rotational position of the bone screw, are known.

U.S. Pat. No. 5,672,176 describes a bone screw with a receiving part with a conically shaped seat and a conically shaped pressure element which exerts a pressure onto the head from above and from the side. If the cone angle has a value laying within a specific range self-locking of the pressure element within the receiving part takes place which allows to preliminary lock the head within a receiving part while the rod is still movable in order to allow the adjustment of its position.

WO 2007/038350 A2 discloses an apparatus for connecting a bone anchor to a support rod, the apparatus including a connector body and a cap. The connector body has a socket for insertion, angulation and removal of a bone anchor. A sleeve is provided which is configured to fit over the connector body in a temporary position, in which the sleeve permits insertion of the bone anchor, to move to a provisional locking position, in which the sleeve permits angulation but prevents removal of the bone anchor, and to move to a locking position, in which the sleeve prevents both angulation and removal of the bone anchor.

U.S. Pat. No. 6,063,090 relates to a device used to connect a longitudinal support to a pedicle screw by an accommodating head having a channel to accommodate the longitudinal support. The pedicle screw and the accommodating head are connected via a conical collet chuck in the accommodating head and by a spherical head on the pedicle screw. The device allows engagement of the pedicle screw in the accommodating head after the pedicle screw has been inserted into the bone.

U.S. Pat. No. 6,132,432 describes a spinal implant fixation assembly including a bone fixation member such as a screw and a rod receiving seat which is operatively connected to the bone fixation element. In one embodiment a screw head receiving insert is provided, which is movable within the assembly between a locked position entrapping the screw head therein and an unlocked position, wherein the screw head enters or escapes.

SUMMARY

It is an object of the invention to provide an improved receiving part for receiving a rod for coupling the rod to a bone anchoring element and a bone anchoring device with such a receiving part. The receiving part may include fewer parts and may be more easily and/or more safely handled during surgery.

A pressure element can be arranged in the receiving part body in three positions. In an insertion position the head is insertable from a bottom of the receiving part body into an accommodation space of the receiving part body. In a pre-locking position, the pressure element pre-locks the head in the accommodation space, which prevents inadvertent removal of the head from the receiving part body and/or inadvertent movement of the head with respect to the receiving part body during surgery. This allows for safer handling of the bone anchoring device during surgery. In a locking position, the head is finally locked in the receiving part. The pressure element can be releasably held in the insertion position and/or in the pre-locking position. This makes handling more convenient.

Pre-locking and final locking of the head are achieved with the same pressure element. Hence, the receiving part and the bone anchoring device according to embodiments of the invention comprise fewer elements, which reduces the costs for manufacturing and which facilitates handling. It makes use of the principle of clamping the head of the bone anchoring element circumferentially from a lateral side, which reduces a force necessary to safely clamp the head. The design of the receiving part allows introduction of the head from the bottom of the receiving part. Such a design may be more readily utilized when a modular system is provided wherein various bone anchors and/or different receiving parts are available prior to surgery.

BRIEF DESCRIPTION OF THE DRAWINGS

Further features and advantages of the invention will become apparent from the description of embodiments using the accompanying drawings. In the drawings:

FIG. 8 shows a cross-sectional view of a bone anchoring device according to the first embodiment with a pressure element in a first position, and when the bone anchoring element is not yet inserted, the section taken perpendicular to the rod axis.

FIG. 9 shows a cross-sectional view of the bone anchoring device according to the first embodiment with the pressure element in the first position and the bone anchoring element partially inserted.

FIG. 10 shows the bone anchoring device of FIG. 9 with the bone anchoring element fully inserted.

FIG. 11 shows a cross-sectional view of the bone anchoring device of the first embodiment with the pressure element in a pre-locking position.

FIG. 12 shows an enlarged view of a detail of FIG. 11.

FIGS. 13a to 13h show various examples of outer and inner cooperating surfaces of the pressure element and the receiving part body, respectively.

FIG. 14 shows the bone anchoring device of FIG. 8 with a rod inserted and the head locked.

FIG. 15 shows an exploded perspective view of a bone anchoring device according to a second embodiment.

FIG. 16 shows an enlarged side view of a pressure element according to the second embodiment.

FIG. 17 shows a cross-sectional view of the pressure element of FIG. 16.

FIG. 18 shows a side view of the pressure element of FIG. 16 rotated by 90°.

FIG. 19 shows a bottom view of the pressure element of FIG. 16.

DETAILED DESCRIPTION OF THE INVENTION

Figure 1:
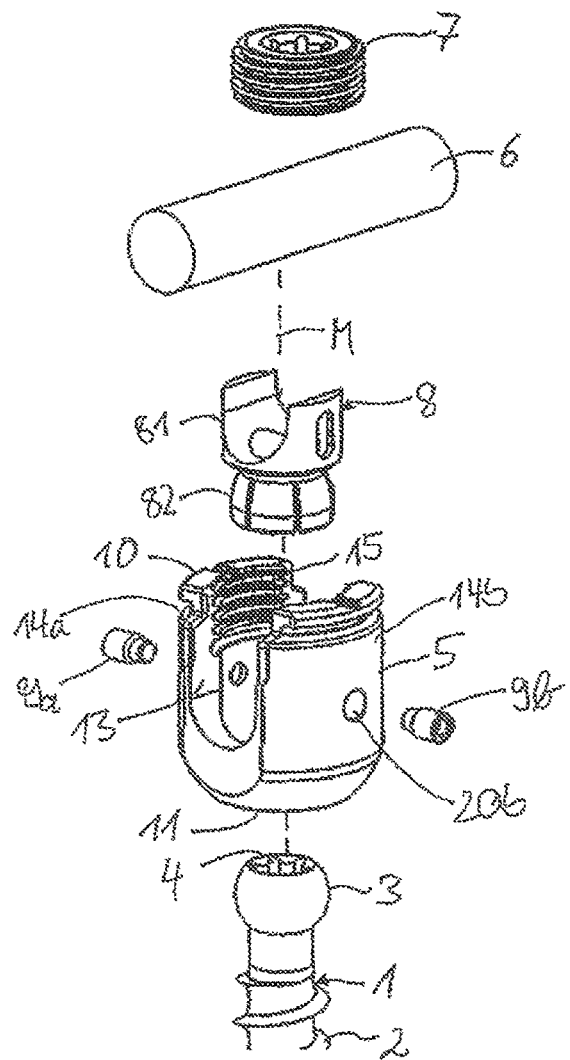
FIG. 1 shows a perspective exploded view of a first embodiment of the bone anchoring device.
Figure 2:
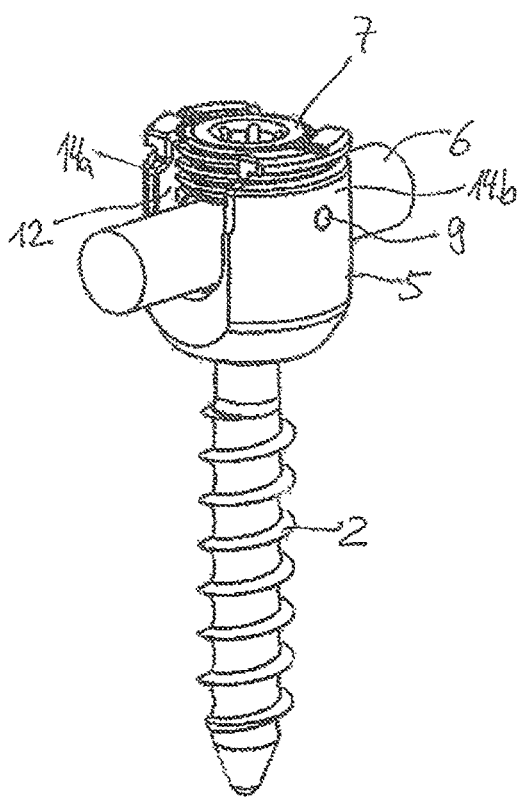
FIG. 2 shows a perspective view of the bone anchoring device of FIG. 1 in an assembled state.
Figure 3:
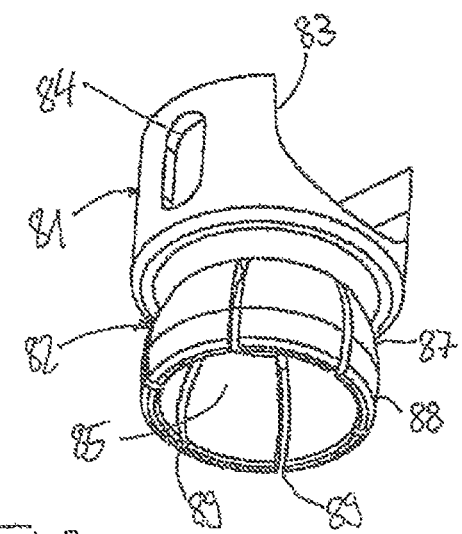
FIG. 3 shows a perspective view of a pressure element according to the first embodiment.

As shown in FIGS. 1 and 2, a bone anchoring device according to a first embodiment comprises a bone anchoring element 1 in the form of a bone screw having a threaded shaft 2 and a head 3, which is in this embodiment a spherical segment-shaped head. The head 3 has a recess 4 for engagement with a screwing-in tool. The bone anchoring device further comprises a receiving part body 5 for receiving a rod 6 to connect the rod 6 to the bone anchoring element 1. Further, a closure element 7 in the form of an inner screw is provided for securing the rod 6 in the receiving part body 5. In addition, the bone anchoring device includes a pressure element 8 for locking the head 3 in the receiving part body 5. The pressure element 8 is held in the receiving part body 5, for example via pins 9a, 9b.

The receiving part body 5 is now explained with reference to FIGS. 1 and 8 to 14. The receiving part body 5 comprises a first end 10 and a second end 11 opposite the first end and an axis of symmetry M passing through the first end and the second end. A bore 12 is provided which is coaxial with the axis of symmetry M. In a first region adjacent to the first end 10, the receiving part body 5 has a U-shaped recess 13, which is symmetric with respect to the axis of symmetry M, the recess 13 having a bottom directed towards the second end 11 and two free lateral legs 14a, 14b extending towards the first end 10. In the region of the legs 14a, 14b an internal thread 15, which cooperates with the inner screw 7, is provided. A channel formed by the U-shaped recess 13 is sized so as to receive the rod 6 therein, the rod to connect a plurality of anchoring devices. At a second region near the second end 11, a cylindrical portion of the bore 12 is followed by a first tapered portion 16 tapering towards the second end 11 with a cone angle. The first tapered portion 16 is followed by a second tapered portion 17 tapering towards the second end 11 with a cone angle smaller than the cone angle of the first tapered portion. An opening 18 is provided at the second end 11. A diameter of the opening 18 is larger than a diameter of the head 3 and smaller than the inner diameter of the bore 12. The coaxial bore 12 provides an accommodation space 19 for the screw head 3.

On each leg 14a, 14b, bores 20a, 20b extending through the legs 14a, 14b are provided for receiving the pins 9a, 9b. The bores 20a, 20b are located approximately at a center of each leg.

Figure 4:
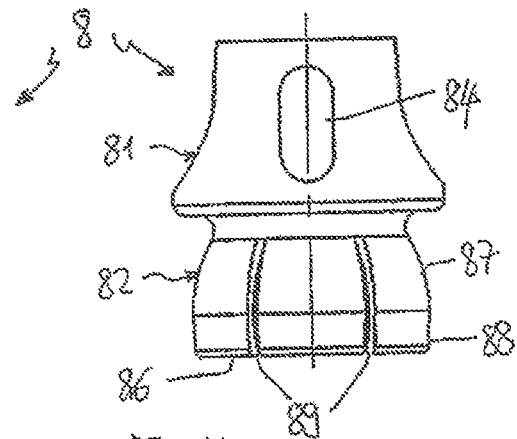
FIG. 4 shows a side view of the pressure element of FIG. 3.
Figure 5:
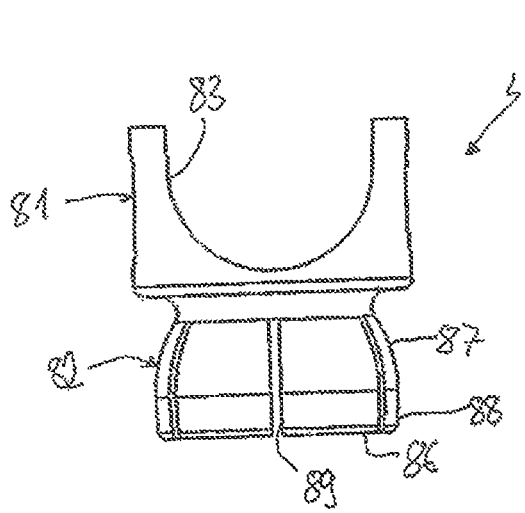
FIG. 5 shows a side view of the pressure element shown in FIG. 4 rotated by 90°.
Figure 6:
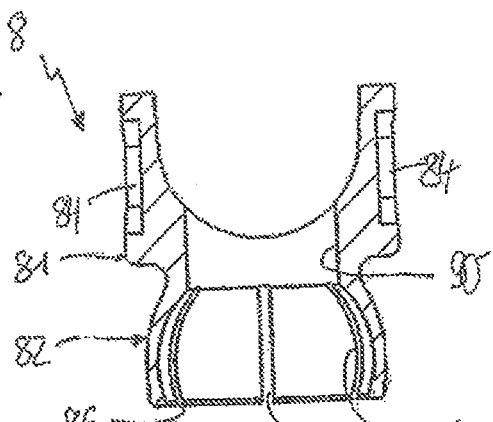
FIG. 6 shows a cross-sectional view of the pressure element shown in FIG. 5.
Figure 7:
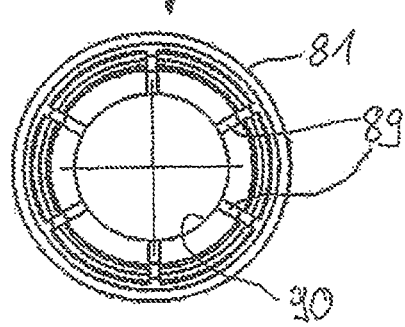
FIG. 7 shows a bottom view of the pressure element shown in FIGS. 3 to 6.

As can be seen in FIGS. 1 and 3 to 7, the pressure element 8 includes a first portion 81, which is substantially cylindrical and which has an outer diameter which is slightly smaller than the inner diameter of the bore 12, so that the pressure element 8 is movable in the bore 12, and a second portion 82 which is recessed with respect to the first portion and which has a maximum outer diameter which is smaller than the inner diameter of the bore 12. The first portion 81 has at its end opposite to the second portion 82 a U-shaped recess 83 for receiving the rod 6 therein when the pressure element 8 is situated in the receiving part body 5. At the lateral sides of the U-shaped recess the pressure element comprises two elongate recesses 84 in the outer wall which are arranged opposite to each other, and which are aligned such that a longer side of the elongate recesses 84 is parallel to the axis of symmetry M of the receiving part body 5. As can be seen in FIG. 4, the width of the lateral sides of the first portion 81 decrease towards the end opposite to the second portion 82 for at least a part of the first portion 81.

The second portion 82 is formed similar to a collar, and comprises a first end at the side of the first portion 81 which is recessed with respect to the first portion 81 and a second end, and a hollow interior 85 which is substantially spherically shaped to clamp the spherical head 3 therein. The second end of the second portion 82 has an opening 86 for introduction of the head 3. An outer wall of the second portion 82 comprises a first portion 87 which is spherical and a second portion 88 adjacent to the opening 86 which is tapered. The tapered portion 88 of the pressure element cooperates with the second tapered portion 17 of the receiving part body. The second portion 82 of the pressure element further comprises a plurality of slits 89 extending from an edge of the opening 86 through the second portion 82. The number and dimensions of the slits 89 are such that the wall of the second portion is flexible enough to snap onto the head 3 when the head 3 is being inserted. Further, the pressure element comprises a coaxial bore 90 for providing access to the screw head 3 by a tool.

As can be seen in FIGS. 8 to 14, since the pressure element has a maximum outer diameter which is slightly smaller than the inner diameter of the bore 12, it can be inserted from the first end 10 of the receiving part body 5 into the receiving part body 5. Once the pressure element 8 is inserted, the pins 9a, 9b are introduced in the bores 20a, 20b so that they engage in the elongate recesses 84, thereby holding the pressure element 8 in the receiving part body 5 and with the U-shaped recess 83 aligned with the U-shaped recess 13 of the receiving part body 5, and preventing escaping of the pressure element through the first end 10. Since the second portion 82 of the pressure element 8 has an outer diameter which is smaller than the inner diameter of the bore 12, and since the second portion 82 of the pressure element has a flexible outer wall, the second portion can expand within the accommodation space 19 when the screw head 3 is introduced.

All parts described before may be made of a bio-compatible material, such as a bio-compatible metal like stainless steel or titanium, or a bio-compatible metal alloy, for example, nitinol, or are made from a bio-compatible plastic material, for example, PolyEtherEtherKetone (PEEK).

The steps of assembling the bone anchoring device are now explained with respect to FIGS. 8 to 14. First, when the pressure element 8 is introduced into the receiving part body 5 and held by the pins 9a, 9b, it is oriented such that the opening 86 is directed towards the second end 11 of the receiving part body 5. As shown in FIG. 8, the pressure element 8 is in its uppermost position which is an insertion position for allowing the screw head 3 to be inserted. In the insertion position, the flexible second portion of the pressure element is positioned freely in the accommodation space 19. The insertion position is limited against upward movement by an abutment which is in this embodiment provided by the engagement of the pins 9a, 9b with the lower end of the recesses 84. As shown in FIG. 9, the screw head 3 is then inserted through the opening 18 into the accommodation space 19, where the second portion 82 of the pressure element 8 is located. The screw head 3 is introduced into the hollow interior 85 of the second portion 82 of the pressure element through the opening 86. Due to the flexibility of the wall provided by the slits 89, the second portion 82 expands in the accommodation space 19 as shown in FIG. 9. The second portion 82 snaps onto the screw head 3 until it encompasses the screw head 3 as shown in FIG. 10. The pins also prevent the pressure element 8 from escaping through the open first end 10 when the screw head 3 is inserted. In the insertion position the screw head 3 is pivotable in the receiving part and also removable if the pressure element remains in this position. There may be means (not shown) for holding the pressure element temporarily in the insertion position. Alternatively, the pressure element can be held in the insertion position by means of a tool (not shown).

FIGS. 11 and 12 show a pre-locking position of the pressure element. When the screw head 3 is inserted and the pressure element 8 is pressed down slightly, the outer wall of the second portion 82 of the pressure element is guided by the first tapered portion 16, so that it contacts the second tapered portion 17 of the receiving part body. The tapered portion 88 of the outer wall of the pressure element 8 and the tapered portion 17 of the receiving part body 5 come into engagement, whereby a pre-stress is exerted by the second portion 82 of the pressure element onto the screw head 3, which pre-locks the head 3. Pre-locking means that under conditions arising during surgery, an angular position of the bone anchoring element 1 with respect to the receiving part body 5 is maintained and can be loosened only by exerting an additional force onto the receiving part body or the bone anchoring element. The pre-locking position of the pressure element can be achieved either manually by pushing down the pressure element, or by inserting the rod and screwing in the inner screw 7 so that the rod presses onto the pressure element thereby moving it slightly downwards.

FIGS. 13a and 13b show the engagement of the outer surface portion of the pressure element and the inner surface portion of the receiving part body in the pre-locking condition. As described before, the surfaces 17, 88 can be tapered as shown in FIG. 13a. Alternatively to, or in addition to, tapered surfaces, portions of the surfaces 88', 17' can be rounded as shown in FIG. 13b. The first tapered portion 16 at the receiving part body 5 serves only for guidance in some embodiments and can be omitted.

Figure 13C:
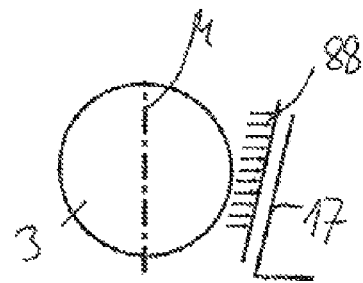
Figure 13D:
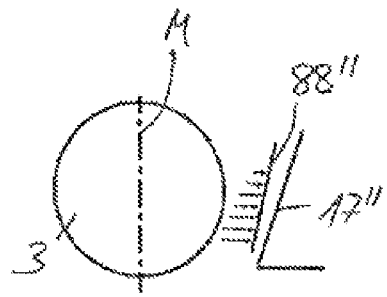
Figure 13E:
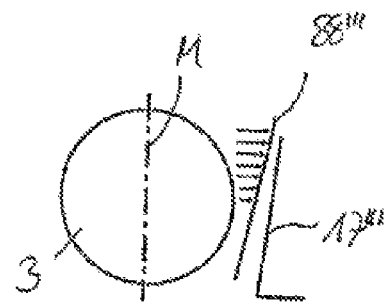
Figure 13F:
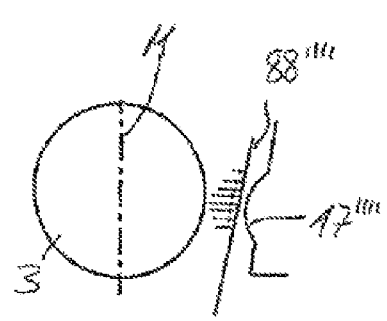

FIGS. 13c to 13h schematically show various examples of engagements of the outer surface portion of the pressure element and the inner surface portion of the receiving part body. In FIG. 13c the two tapered portions 17, 88 are tapered at substantially a same angle. This provides a substantially even pressure distribution (approximated by arrows) between the second portion 88 of the pressure element and the tapered portion 17 of the receiving part body. FIGS. 13d and 13e show two different variations where the portions are tapered at different angles. FIG. 13d shows a main contact area at the bottom of portion 17" and FIG. 13e shows a main contact area at the top of portion 17'". FIG. 13f shows a tapered portion 88"" of the pressure element and a rounded or curved portion 17"" of the receiving part body, wherein the curvature is directed towards the center of the receiving part body. With such a configuration, a focused contact area at the rounded portion can be achieved.

Figure 13G:
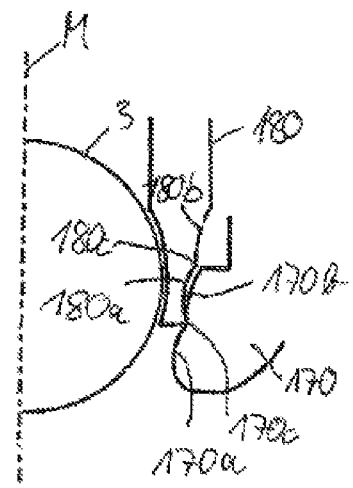
Figure 13H:
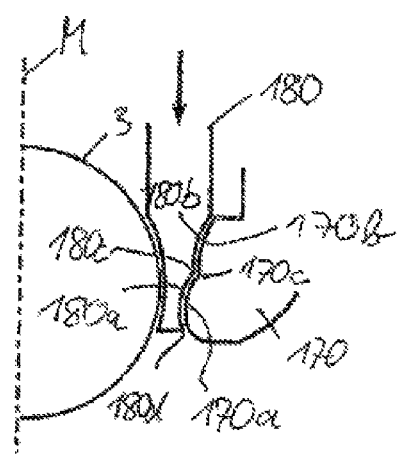

In FIGS. 13g and 13h the narrowing portion 170 of a modified example of the receiving part body 5 has a double spherical radius formed by two curved portions 170a and 170b adjacent to each other with a groove 170c therebetween. The curvatures are directed to a central axis M. A modified pressure element 180 has at its lower end two correspondingly curved portions 180a and 180b which correspond to the curved portions 170a and 170b, with a crest 180c therebetween, and an outer crest 180d at an outer edge of the pressure element 180.

As shown in FIG. 13g, when the pressure element 180 moves downwards, its lowermost edge 180d engages in the groove 170c. In this position, there is a frictional clamping of the head 3, which still allows the head 3 to be pivoted upon exertion of a force which is greater than the force needed to pivot the head 3 when the head 3 is introduced in the insertion position. This is an example of the pre-locking condition. As shown in FIG. 13h, by pressing the pressure element 180 further downward, the respective curvatures 180a, 180b of the pressure element 180 engage with the corresponding curvatures 170a, 170b of the narrowing portion 170 to lock the head 3.

The third position of, for example, the embodiment of FIG. 8, which is a locking position, is shown in FIG. 14. The locking position is defined as the position in which the screw head 3 is locked in the receiving part body 5. In this position, the tapered outer surface portion 88 of the pressure element engages the second tapered portion 17 of the receiving part body over a larger area. Thereby, the flexible wall of the second portion 82 of the pressure element 8 is pressed onto the head 3 so that the head 3 is locked. This position is achieved by further tightening the inner screw 7, thereby further pressing down the rod 6.

In use, the bone anchoring device can be, for example, pre-assembled in such a way that a suitable bone anchoring element 1 is selected and introduced into the receiving part body 5 with an inserted pressure element 8. The bone anchoring device can be brought into the pre-locking condition by slightly pushing down the pressure element 8. Then, the screw element 1 is screwed into the bone. The recess 4 of the head 3 can be accessed with a screw tool through the coaxial bore 12 and the bore 90. To correctly align the receiving part with respect to the rod to which it shall be connected, an additional force is exerted onto the receiving part either manually or by application of an instrument. Once a desired position of the rod with respect to other bone anchoring devices is achieved, the inner screw 7 is tightened, thereby shifting down the pressure element into the locking position. A final tightening of the inner screw locks the rod and the head substantially simultaneously.

The bone anchoring device can be pre-assembled either by the manufacturer or in the course or preparation of surgery, or at any other time. In one embodiment, the surgeon can select the desired receiving parts and bone anchoring elements prior to surgery according to specific details of the particular clinical application. The design of the bone anchoring device allows selection of an appropriate bone anchoring element in terms of diameter, length, and other features. Hence, a modular system is provided which includes various receiving parts and several bone anchoring elements, which then individually can be chosen and adapted.

A second embodiment of the bone anchoring device is now described with respect to FIGS. 15 to 26. Parts which are similar to those of the first embodiment have the same reference numerals, and the descriptions thereof will not be repeated. The second embodiment of the bone anchoring device differs from the first embodiment in the design of the pressure element and the pins. The first portion 81' of the pressure element 8' differs from the first portion 81 of pressure element 8. The first portion 81' of the pressure element 8' has a shallow recess 83' which is curved in a substantially cylinder segment shape for guiding the rod 6. It further includes two upstanding resilient fingers 91*a*, 91*b* extending from respective lateral sides of the recess 83' in the direction of the first end 10 of the receiving part body. The fingers 91*a*, 91*b* have outwardly directed portions 92 at their free ends, respectively. An outer diameter of the first portion 81' at least in the region of the fingers, is smaller than the inner diameter of the bore of the receiving part body, such that the resilient fingers 91*a*, 91*b* can move.

Figure 20:
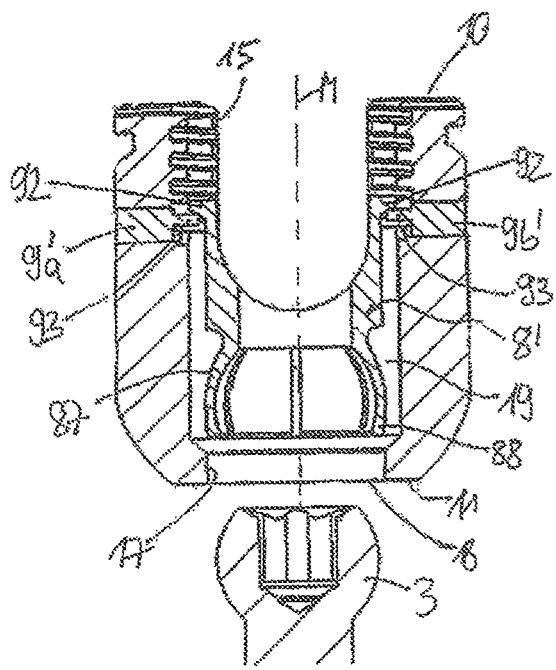
FIG. 20 shows a cross-sectional view of the bone anchoring device according to the second embodiment with the pressure element in an insertion position and the bone anchoring element not yet inserted, the cross-section taken perpendicular to the rod axis.
Figure 21:
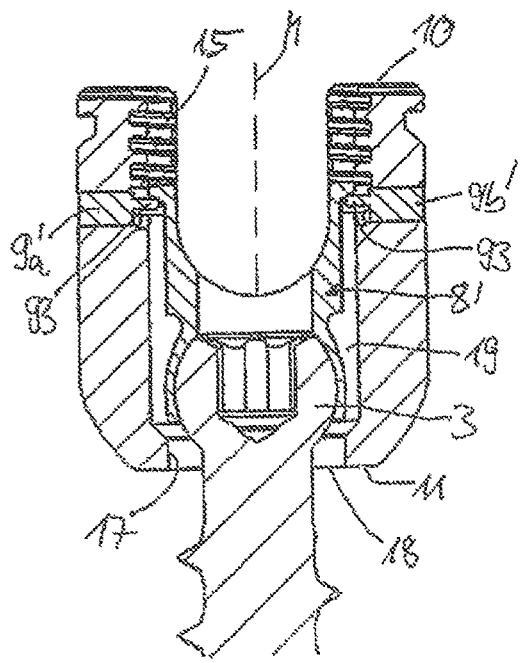
FIG. 21 shows the bone anchoring device of FIG. 20 with the bone anchoring element fully inserted.

Pins 9*a'*, 9*b'* each have a flattened portion 93, a width of which is substantially the same as a width of the outwardly extending portions 92 of the resilient fingers 91*a*, 91*b*. When the pins 9*a'*, 9*b'* are inserted into the bores 20*a*, 20*b*, the portions 93 extend into the coaxial bore 12 of the receiving part body 5 as shown in FIG. 20. In this manner, an abutment is provided for the receiving part 8'.

Figure 22:
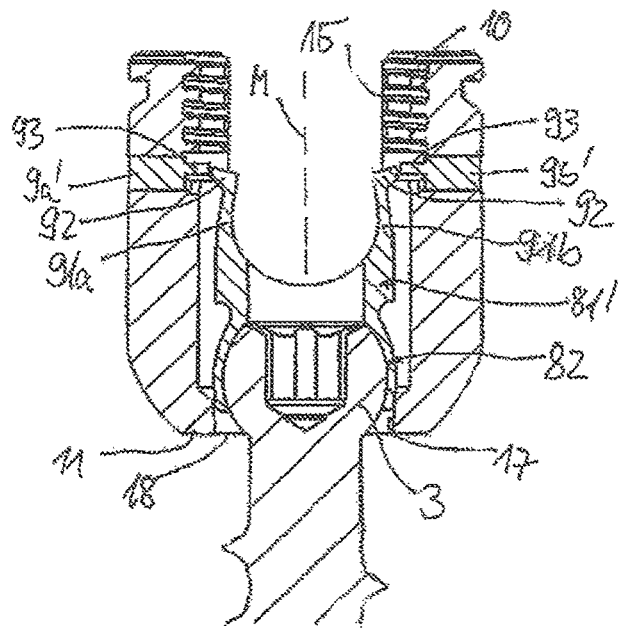
FIG. 22 shows the bone anchoring device of FIG. 20 with the pressure element in a position just before a pre-locking position.
Figure 23:
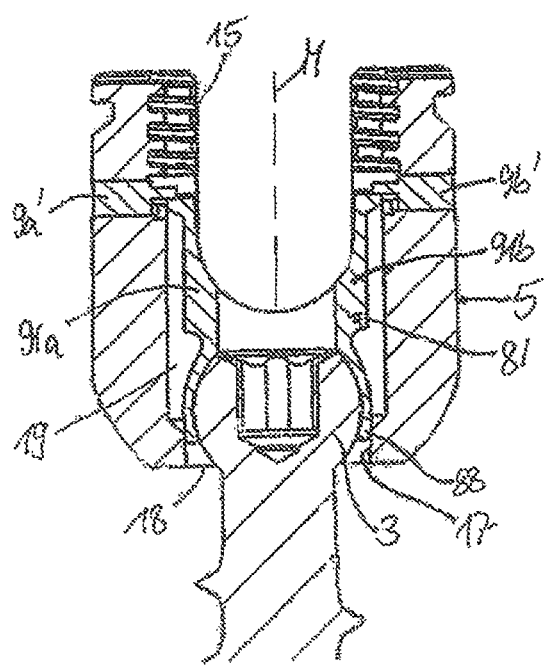
FIG. 23 shows the bone anchoring device of FIG. 20 with the pressure element in the pre-locking position.
Figure 24:
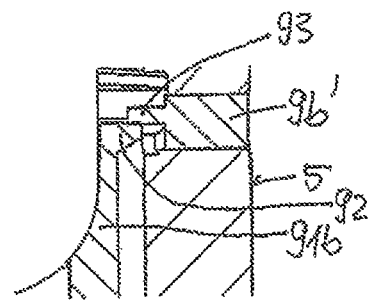
FIG. 24 shows an enlarged view of a portion of FIG. 23.
Figure 25:
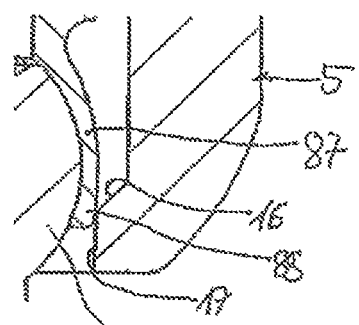
FIG. 25 shows an enlarged view of another portion of FIG. 23.

The assembly of the bone anchoring device according to the second embodiment is explained with respect to FIGS. 20 to 25. In FIG. 20, first, the pressure element 8' is inserted from the first end 10 into the receiving part body 5. Then the pins 9*a'*, 9*b'* are inserted into the holes in the legs. The pressure element 8' is in such a position that the outwardly extending portions 92 of the resilient fingers 91*a*, 91*b* are located above the flattened portions 93 of the pins 9*a'*, 9*b'*. In this position the pressure element 8' is in an insertion position. Then, the screw head is inserted through the openings 18 and 86 until the second portion 82 of the pressure element 8' is around the screw head 3. Then, as shown in FIG. 22, the pressure element 8' is moved slightly downward to enter a pre-locking position. Here, the resilient fingers 91*a*, 91*b* are first pressed inwards for the outwardly extending portion 92 to move past the flattened portion 93 of the pins. As shown in FIG. 23, the outwardly extending portions 92 then move outward and the flattened portions 93 form an abutment for the pressure element. In this pre-locking position, the tapered outer surface portion of the second portion 82 engages the tapered portion 17 of the receiving part body. Since the pins 9*a'*, 9W act as a stop, the pre-locking position is secured (i.e., the pressure element 8' does not move back to the insertion position).

Figure 26:
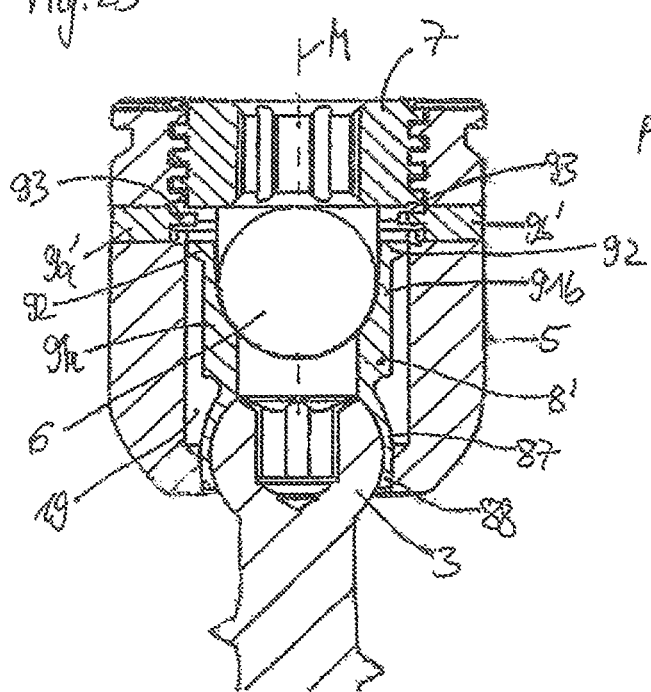
FIG. 26 shows the bone anchoring device of FIG. 20 with the pressure element in the locking position and the head locked.

Inserting the rod and screwing in the inner screw 7 moves the pressure element further down until it achieves a final locking position as shown in FIG. 26.

The clinical use of the bone anchoring device is similar to that of the first embodiment.

Further modifications of the embodiments shown are possible. For example, the head of the bone anchoring element can have any other shape, for example, a cylindrical shape whereby a monoaxial bone screw is provided allowing rotation of the screw element with respect to the receiving part around a single axis. The head 3 can also be, for example, conically shaped, where the hollow interior portion 85 of the pressure element is adapted to this shape. In a further modification, the receiving part body 5, or at least the second portion 82 of the pressure element, is made of a bio-compatible plastic material which provides elasticity to a certain degree. In this case, the slits may be omitted.

Alternatively to the second embodiment a spring portion can be provided, for example in the receiving part body, which may cooperates with a portion of the pressure element. Generally, the pins are only one example of achieving an abutment for the pressure element. Other constructions such as snap rings or various other features may also be utilized.

In one embodiment, the receiving part body can have an inclined open end to allow a greater angulation of the head in one direction.

In one embodiment, the outer surface of the second portion 82 of the pressure element can be tapered, and the second tapered portion 17 of the receiving part body can be inwardly curved.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
   a receiving part body having a first end and a second end below the first end, a channel that opens towards the first end for receiving the rod, an engagement structure on an inner wall of the receiving part body at the first end that is configured to receive a closure element for securing the rod in the channel, an accommodation space for accommodating a head of the bone anchoring element, and an opening at the second end for inserting the head into the accommodation space; and
   a pressure element comprising a first portion configured to be positioned in the channel when the pressure element is in the receiving part body and a second portion axially connected to the first portion and having an expandable portion defining a hollow section and an opening,
   wherein the pressure element is configured to assume an inserting position, where at least part of the expandable portion is positioned in the accommodation space and spaced apart from the inner wall of the receiving part body, and where the pressure element engages a first portion of the inner wall of the receiving part body to hold the pressure element against upward movement towards the first end of the receiving part body, wherein the pressure element is movable downwards axially away from the inserting position to a pre-locking position, where the expandable portion contacts the inner wall of the receiving part body, and where the pressure element engages an abutment on the inner wall of the receiving part body that faces downwards towards the second end of the receiving part body to hold the pressure element against upward movement back towards the inserting position, the abutment on the inner wall being spaced apart axially from and distinct from the engagement structure, and wherein the pressure element is movable further downwards axially away from the pre-locking position to a locking position, where the receiving part body contacts and applies a radially inwardly directed pressure on two diametrically opposite regions of an outer wall of the expandable portion.

2. The receiving part of claim 1, wherein the first portion of the inner wall of the receiving part body comprises a stop that is configured to contact the pressure element in the inserting position.

3. The receiving part of claim 1, wherein the pressure element is held in the pre-locking position by a spring force.

4. The receiving part of claim 3, wherein the spring force is generated by a spring portion on the pressure element which cooperates with the abutment on the inner wall of the receiving part body.

5. The receiving part of claim 1, wherein a portion of the receiving part body that defines the accommodation space is substantially cylindrical and has a narrowing portion that narrows towards the opening of the receiving part body.

6. The receiving part of claim 5, wherein the pressure element comprises a narrowing portion on the outer wall which cooperates with the narrowing portion of the receiving part body.

7. The receiving part of claim 6, wherein at least one of the narrowing portion of the receiving part body or the narrowing portion of the pressure element is tapered.

8. The receiving part of claim 7, wherein the respective narrowing portions of the receiving part body and the pressure element are tapered at substantially a same angle.

9. The receiving part of claim 7, wherein the respective narrowing portions of the receiving part body and the pressure element are tapered at different angles.

10. The receiving part of claim 7, wherein the other one of the narrowing portion of the receiving part body or the narrowing portion of the pressure element is curved or rounded.

11. The receiving part of claim 10, wherein the narrowing portion of the receiving part body and the narrowing portion of the pressure element are curved or rounded.

12. The receiving part of claim 11, wherein the narrowing portion of the receiving part body comprises two adjacent curved portions having convex curvatures directed towards a central axis of the receiving part and forming a groove therebetween, and wherein the narrowing portion of the pressure element comprises two adjacent curved portions having concave curvatures corresponding to the convex curvatures of the two curved portions of the receiving part body, respectively, and forming a crest therebetween.

13. The receiving part of claim 12, wherein in the pre-locking position an edge of the pressure element engages the groove of the receiving part body, and wherein in the locking position the crest of the pressure element engages the groove of the receiving part body.

14. The receiving part of claim 1, wherein the second portion of the pressure element has a smaller maximum outer diameter than a maximum outer diameter of the first portion of the pressure element.

15. The receiving part of claim 1, wherein the pressure element is secured from removal from the receiving part body.

16. The receiving part of claim 1, wherein in the pre-locking position, the outer wall of the expandable portion of the pressure element engages the inner wall of the receiving part body.

17. The receiving part of claim 1, wherein an end of the second portion of the pressure element adjacent to the first portion of the pressure element has an outer diameter that is recessed with respect to an outer diameter of the first portion.

18. The receiving part of claim 1, wherein the hollow section of the expandable portion of the pressure element is for accommodating the head, and the opening of the expandable portion of the pressure element is for inserting the head.

19. The receiving part of claim 1, wherein at least part of the pressure element has a continuous exterior surface portion forming a ring.

20. A bone anchoring device comprising:
a bone anchoring element having a shaft and a head; and
a receiving part for receiving a rod for coupling the rod to the bone anchoring element, the receiving part comprising:
a receiving part body having a first end and a second end below the first end, a channel that opens towards the first end for receiving the rod, an engagement structure on an inner wall of the receiving part body at the first end that is configured to receive a closure element for securing the rod in the channel, an accommodation space for accommodating the head of the bone anchoring element, and an opening at the second end for inserting the head into the accommodation space; and
a pressure element comprising a first portion configured to contact the rod and a second portion axially connected to the first portion and having an expandable portion configured to accommodate and clamp the head,
wherein the pressure element is configured to assume an inserting position, where the head of the bone anchoring element is insertable from the opening of the receiving part body into the pressure element, and where the pressure element engages a first portion of the inner wall of the receiving part body to hold the pressure element against upward movement towards the first end of the receiving part body,
wherein the pressure element is movable downwards axially away from the inserting position to a pre-locking position, where the receiving part prevents removal of the head of the bone anchoring element through the opening, and where the pressure element engages an abutment on the inner wall of the receiving part body that faces downwards towards the second end of the receiving part body to hold the pressure element against upward movement back towards the inserting position, the abutment on the inner wall being spaced apart axially from and distinct from the engagement structure, and wherein the pressure element is movable further downwards axially away from the pre-locking position to a locking position, where the receiving part body contacts and applies a radially inwardly directed pressure on two diametrically opposite regions of an outer wall of the expandable portion to lock the head of the bone anchoring element in the receiving part.

21. The bone anchoring device of claim 20, further comprising:
   the rod; and
   the closure element for securing the rod in the channel of the receiving part body.

22. The bone anchoring device of claim 20, wherein the head is insertable into and removable from the receiving part body when the pressure element is in the inserting position.

23. A method of coupling a rod to a bone via a bone anchoring device, the bone anchoring device comprising a bone anchoring element having a shaft and a head, a receiving part comprising a receiving part body having a first end and a second end below the first end, a channel that opens towards the first end for receiving the rod, an engagement structure on an inner wall of the receiving part body at the first end that is configured to receive a closure element for securing the rod in the channel, an accommodation space for accommodating the head of the bone anchoring element, and an opening at the second end for inserting the head into the accommodation space, a pressure element comprising a first portion configured to contact the rod and a second portion axially connected to the first portion and having an expandable portion configured to accommodate and clamp the head, and a closure element, the method comprising:
   inserting the bone anchoring element into a bone;
   inserting the head of the bone anchoring element through the opening of the receiving part body and into the expandable portion of the pressure element when the pressure element is in an inserting position where the pressure element engages a first portion of the inner wall of the receiving part body to hold the pressure element against upward movement towards the first end of the receiving part body;
   moving the pressure element downwards axially away from the inserting position to a pre-locking position, where the receiving part prevents removal of the head of the bone anchoring element through the opening, and where an engagement between the pressure element and an abutment on the inner wall of the receiving part body that faces downwards towards the second end of the receiving part body holds the pressure element against upward movement back towards the inserting position, the abutment on the inner wall being spaced apart axially from and distinct from the engagement structure;
   adjusting an angular position of the receiving part relative to the bone anchoring element;
   inserting the rod into the channel of the receiving part body; and
   advancing the closure element in the channel to push the rod against the pressure element to move the pressure element further downwards axially away from the pre-locking position to a locking position, where the receiving part body contacts and applies a radially inwardly directed pressure on two diametrically opposite regions of an outer wall of the expandable portion, to lock respective positions of the head of the bone anchoring element and the rod relative to the receiving part.

24. The method of claim 23, wherein a shape of the first portion of the pressure element remains constant when the head of the bone anchoring element is introduced into the expandable portion of the pressure element.

\* \* \* \* \*

UNITED STATES PATENT AND TRADEMARK OFFICE
CERTIFICATE OF CORRECTION

PATENT NO. : 10,182,848 B2  
APPLICATION NO. : 14/517624  
DATED : January 22, 2019  
INVENTOR(S) : Biedermann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this
Tenth Day of December, 2019

Andrei Iancu
*Director of the United States Patent and Trademark Office*